United States Patent [19]

Takahashi et al.

[11] Patent Number: 5,136,066
[45] Date of Patent: Aug. 4, 1992

[54] PROCESS FOR PREPARING OPTICALLY ACTIVE CYCLOPENTENONE DERIVATIVE

[75] Inventors: Takashi Takahashi, Kanagawa; Yoshikazu Takehira, Hyogo, both of Japan

[73] Assignee: Daiso Co., Ltd., Osaka, Japan

[21] Appl. No.: 727,260

[22] Filed: Jul. 9, 1991

[51] Int. Cl.$^5$ .................. C07F 7/04; C07C 67/297; C07C 69/145
[52] U.S. Cl. .................. 556/436; 556/427; 568/666
[58] Field of Search ............. 556/427, 436, 442; 568/579, 596, 666

[56] References Cited

PUBLICATIONS

Alverez et al. JACS, 94, 7823 (1972).
Kluge et al. JACS, 94, 7828 (1972).
Kluge et al. JACS, 94, 9256 (1972).
Sih et al. JACS, 97, 857, (1975).
Sih et al. JACS 97 865 (1975).
Stork et al., JACS 97 4745 (1975).

Primary Examiner—Jose G. Dees
Assistant Examiner—Joseph Conrad
Attorney, Agent, or Firm—Armstrong, Nikaido, Marmelstein, Kubovcik & Murray

[57] ABSTRACT

The present invention provides a process for preparing an optically active cyclopentenone derivative represented by the formula

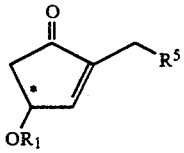

(XI)

by oxidizing an optically active cyclopentanone derivative represented by the formula

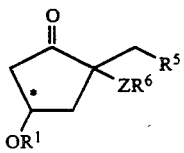

(X)

with an oxidizing agent, and subsequently subjecting the oxidized compound to an elimination reaction. (In the above formulae, $R^1$ is a protective group for hydroxyl, $R^5$ is straight-chain or branched alkyl, alkenyl, alkynyl or alkylaryl having 5 to 22 carbon atoms and containing or not containing oxygen, sulfur or silicon, $R^6$ is alkyl, aryl or heterocyclic group having or not having a substituent, Z is selenium or sulfur, and the symbol * represents an asymmetic carbon atom.)

6 Claims, No Drawings

PROCESS FOR PREPARING OPTICALLY ACTIVE CYCLOPENTENONE DERIVATIVE

FIELD OF THE INVENTION

The present invention relates to a process for preparing optically active cyclopentenone derivatives which are useful as materials for producing prostaglandins.

DESCRIPTION OF THE PRIOR ART

Processes heretofore known for preparing optically active prostaglandins include one wherein Corey lactone is used as the starting material, and one wherein 4-hydroxycyclopentenone is used as the starting material. However, the former process requires many steps, consequently giving the final product in a low yield, whereas the latter process has the problem that it is relatively difficult to determine the reaction conditions for effecting the main reaction in preference by inhibiting the side reaction.

We have conducted intensive research in order to overcome the above problems and developed a process for preparing with ease and in a high yield an optically active cyclopentenone derivative which is a key intermediate for the production of a prostagladin and which is represented by the formula

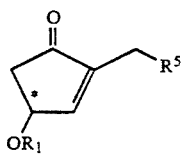 (XI)

The present invention provides this novel process for preparing the optically active cyclopentenone derivative (XI).

SUMMARY OF THE INVENTION

The main object of the present invention is to provide a novel process for preparing optically active cyclopentenone derivatives (XI) which are key intermediates for producing prostaglandins so as to obtain prostaglandins by a greatly simplified process in a high yield without resorting to cumbersome procedures unlike the above-mentioned processes wherein Corey lactone or 4-hydroxycyclopentenone is used as the starting material.

According to the present invention, the optically active cyclopentenone derivative of the formula (XI) is prepared by oxidizing an optically active cyclopentanone derivative represented by the formula

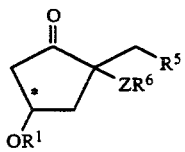 (X)

with an oxidizing agent, and subsequently subjecting the oxidized compound to an elimination reaction.

The optically active cyclopentanone derivative (X) is prepared by reacting an optically active 2-methylenecyclopentanone derivative represented by the formula

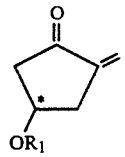 (IX)

with an organozinc or copper compound represented by the formula

$R^5M$ and causing an organoselenium or sulfur compound represented by the formula

$R^6ZY$ to act on the resulting enolate.

The optically active 2-methylenecyclopentanone derivative (IX), which is the starting material of the process of the invention is prepared by the following process.

First, a 2-halogenoacetal derivative represented by the formula

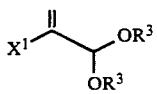 (I)

is reacted with an optically active epoxy compound represented by the formula

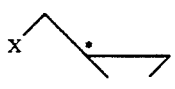 (Ia)

in the presence of a base to obtain an optically active 4-hydroxypentane derivative

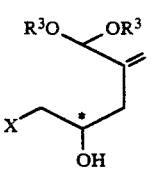 (II)

and the hydroxyl group of the compound (II) is protected with a protective group to obtain an optically active compound represented by the formula

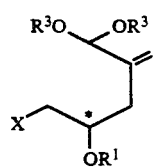 (III)

Next, the acetal portion of the compound (III) is hydrolyzed to convert the compound (III) to an optically active 2-methylenepentanal derivative represented by the formula

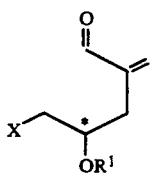
(IV)

The compound (IV) is then converted to an optically active cyanohydrin derivative represented by the formula

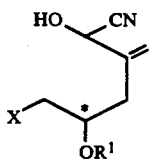
(VI)

Alternatively, the compound (IV) can be readily converted to the cyanohydrin derivative (VI) by reacting the compound (IV) with trimethylsilyl cyanide in the presence of 18-Crown ether-6 catalyst to obtain a trimethylsilylated cyanohydrin derivative represented by the formula

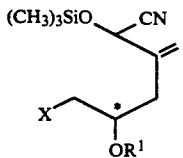
(V)

and hydrolyzing the derivative (V). The compound (V) can be directly made into a compound (VIII) to be described later.

The compound (VI) is converted to a protected cyanohydrin derivative represented by the formula

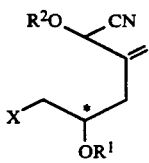
(VII)

by introducing a protective group $R^2$ into the hydroxyl group of the compound (VI).

The compound (VII) is treated in the presence of a base for ring closure and thereby converted to an optically active 2-methylenecyclopentane derivative represented by the formula

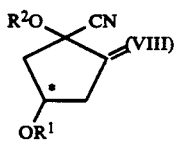
(VIII)

The compound (VIII) is treated in the presence of an acid to hydrolyze the —$OR^2$ group thereof and then treated in the presence of a base for decyanohydrogenation, giving an optically active 2-methylenecyclopentanone derivative (IX).

In the above formulae, $R^1$ is a protective group for hydroxyl, $R^2$ and $R^3$ are each a protective group for hydroxyl, X is a halogen atom or $R^4SO_3$ group (wherein $R^4$ is alkyl or aryl), $X^1$ is a halogen atom, $R^5$ is straight-chain or branched alkyl, alkenyl, alkynyl or alkylaryl having 5 to 22 carbon atoms and containing or not containing oxygen, sulfur or silicon, M is $(CH_3)_2ZnLi$ or a group selected from the group consisting of $Cu(CN)Li$, $Cu(CN)MgBr$, $Cu(CN)MgCl$, $Cu(CN)MgI$, $(CuLi)1/2$, (2-thienyl)$Cu(CN)Li_2$ and $Cu(PBu_3)_n$ (wherein n is 2 to 3, and Bu is butyl), $R^6$ is alkyl, aryl or heterocyclic group having or not having a substituent, Z is selenium or sulfur, Y is a halogen atom or $ZR^6$, and the symbol * stands for an asymmetric carbon atom.

DETAILED DESCRIPTION OF THE INVENTION

The above groups of the compounds for use in the present invention will be described.

The protective group $R^1$ is preferably alkenyl, aralkyl, alkyloxyalkyl, cyclic alkyl having a heteroatom or silyl, and is more preferably silyl.

The protective group $R^2$ is preferably alkyloxyalkyl, cyclic alkyl having a hetero-atom or sinyl, and is more preferably 1-alkyloxyethyl. The protective group $R^2$ may be the same as or different from the protective group $R^1$. More specific examples of protective groups $R^1$ and $R^2$ are allyl as an alkenyl group; benzyl, p-methoxybenzyl, diphenylmethyl and trityl as aralkyl groups; methoxymethyl, benzyloxymethyl, tert-butoxymethyl, 2,2,2-trichloroethoxymethyl, 2-methoxyethoxymethyl and like alkyloxymethyl groups, and 1-ethoxyethyl, 1-methylmethoxyethyl, 1-isopropoxyethyl and like 1-alkyloxyethyl groups as alkyloxyalkyl groups; tetrahydropyranyl and tetrahydrofuranyl as cyclic alkyl groups having a hetero-atom; and trimethylsilyl, triethylsilyl, tert-butyldimethylsilyl, tert-butyldiphenylsilyl, methylditert-butylsilyl, triphenylsilyl, phenyldimethylsilyl, triphenylmethyldimethylsilyl and the like as silyl groups.

Examples of protective groups $R^3$ are methyl, ethyl, 2,2,2-trichloroethyl and like alkyl groups, and benzyl and like aralkyl groups. Examples of cyclic acetals formed by two groups $R^3$ attached to each other are as follows.

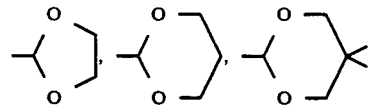

The protective group $R^3$ is preferably alkyl, and is more preferably ethyl.

The group $R^5$ is straight-chain or branched alkyl, alkenyl, alkynyl or alkylaryl which has 5 to 22 carbon atoms and which may contain oxygen, sulfur or silicon. Such groups $R^5$ include alkoxyl, alkyloxyalkoxyl, cyclic or noncyclic acetal, silyl and alkylthio group.

Preferred examples of group $R^5$ are groups represented by the following formulae.

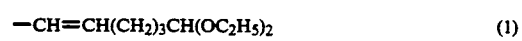 (1)

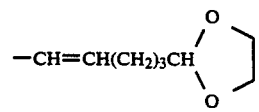 (2)

-continued

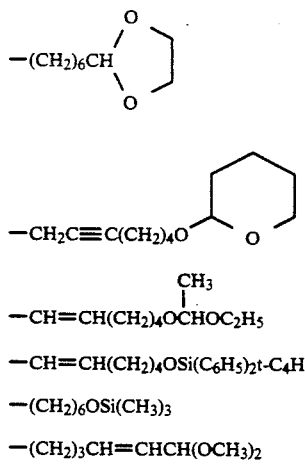

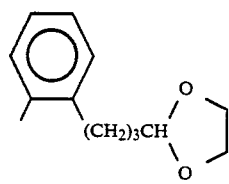

(3)
(4)
(5)
(6)
(7)
(8)
(9)

-continued

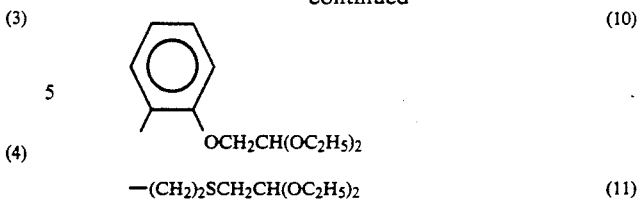

(10)

—(CH$_2$)$_2$SCH$_2$CH(OC$_2$H$_5$)$_2$ (11)

Among these, the group of the formula (5) is more preferred.

Examples of groups R$^6$ are preferably methyl, ethyl and like alkyl groups, phenyl, p-tolyl, p-chlorophenyl and like aryl groups, and 2-pyridyl and like heterocyclic groups, among which phenyl is more preferable.

Examples of X's are halogen atoms; methanesulfonyloxy, trifluoromethanesulfonyloxy and like alkylsulfonyloxy groups; benzenesulfonyloxy, p-toluenesulfonyloxy, m-trifluoromethylbenzenesulfonyloxy, m-chlorobenzenesulfonyloxy and like arylsufonyloxy groups; etc.

Halogen atoms represented by X$^1$, X and Y are chlorine atom, bromine atom, iodine atom and the like.

According to the present invention, the optically active cyclopentenone derivative (XI) which is an intermediate for preparing a prostaglandin is prepared by the process represented by the following reaction scheme.

Reaction Scheme

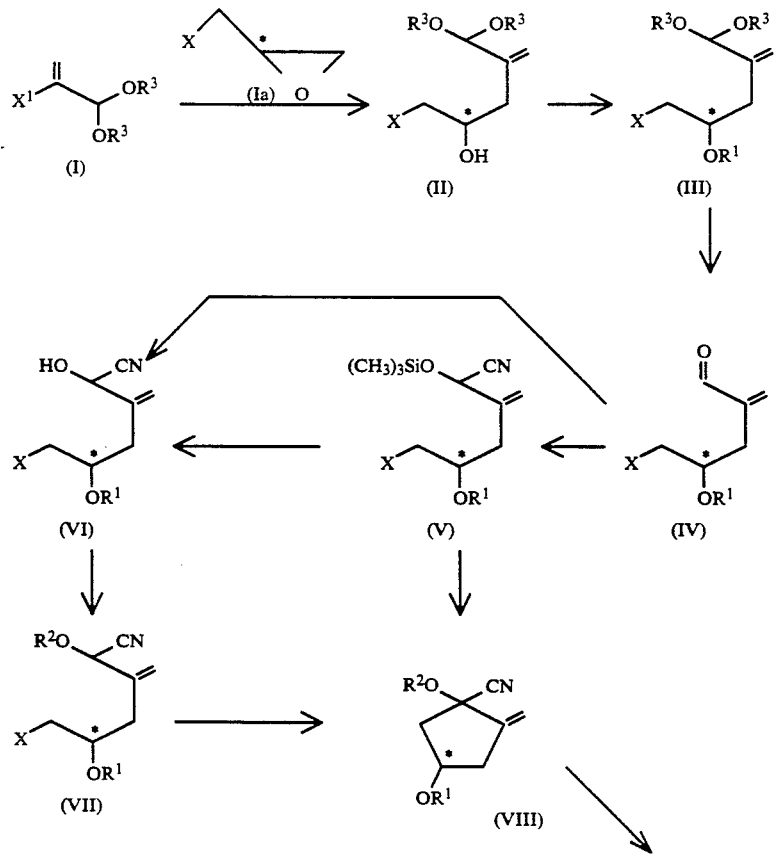

Reaction Scheme

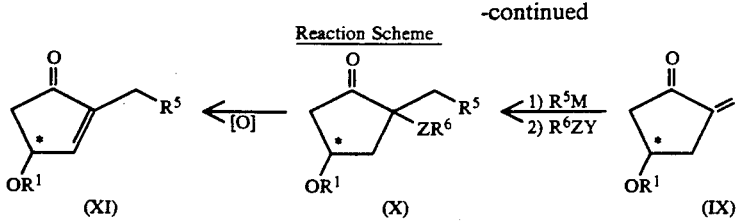

The reactions involved in the above process will be described below.

a) An acetal derivative (I) of 2-halogenoacrylic aldehyde which is known by Tetrahedron Lett., 4797 (1969) is reacted with a strong base, such as methyllithium, n-butyllithium, sec-butyllithium or tert-butyllithium in an amount at least equivalent thereto to prepare a vinyl anion solution. Examples of useful reaction solvents are tetrahydrofuran, diethyl ether, ethylene glycol diethyl ether and like ethers, and hexane and like hydrocarbons.

Next, an optically active epoxy compound (Ia) is reacted with the anion in the presence of a Lewis acid, such as trifluoroboron etherate, to obtain an optically active 4-hydroxy-2-methylenepentane derivative (II). This reaction is conducted preferably at a low temperature of $-30°$ to $-100°$ C. Although the reaction proceeds in the absence of a catalyst, the Lewis acid, if used, effects the reaction at an accelerated velocity.

b) The compound, (II) is converted to an optically active 2-methylenepentane derivative (III) by introducing a protective group $R^1$ into the hydroxyl of the compound. When the group $R^1$ is, for example, alkenyl, aralkyl, alkyloxymethyl or silyl, corresponding $R^1Y^1$(- wherein $Y^1$ a halogen atom such as chlorine, bromine or iodine) is reacted with the compound (II) in an amount of at least one mole per mole of the compound in the presence of at least one mole of a base per mole of the compound (II). Examples of useful bases are triethylamine, ethyldiisopropylamine, pyridine, 4-dimethylaminopyridine, imidazole and like organic bases, and sodium hydride, sodium amide and like inorganic bases. When $R^1$ is a 1-alkyloxyethyl group or cyclic alkyl group having a hetero-atom, the reaction is conducted using at least one mole of corresponding vinyl ether or the like per mole of the compound (II), and an acid catalyst such as hydrogen chloride, p-toluenesulfonic acid, pyridine-p-toluenesulfonic acid salt or an acidic ion exchange resin (such as Amberlyst H15).

c) The compound (III) is made into an optically active 2-methylenepentanal derivative (IV) by hydrolyzing the acetal portion of the compound in the presence of a weak Lewis acid. This reaction can be conducted by reacting the compound (III) with a weak Lewis acid catalyst, such as copper sulfate, zinc bromide or silica gel, in a water-containing solvent, such as a mixture of water and ethanol.

d) The compound (IV) is converted to an optically active cyanohydrin derivative (VI). The conversion to the cyanohydrin derivative is effected using hydrogen cyanide in the usual manner.

Alternatively, the compound (IV) can be readily converted to the compound (VI) by reacting the compound (IV) with trimethylsilyl cyanide in the presence of 18-Crown ether-6 catalyst to obtain a trimethylsilylated cyanohydrin derivative (V), and hydrolyzing the derivative. The compound (V) can be made directly into the compound (VIII) to be described below.

e) A protective group $R^2$ is introduced into the hydroxyl of the compound (VI), whereby the compound is converted to a protected cyanohydrin derivative (VII). The introduction of protective group $R^2$ is done under the same conditions as the introduction of protective group $R^1$ for the conversion of the compound (II) to the compound (III).

f) The compound (VII) is cyclized by being treated in the presence of a base for conversion to an optically active 2-methylenecyclopentane derivative (VIII). Examples of useful bases are lithium hydride, sodium hydride, potassium hydride, lithium amide, sodium amide, potassium amide, lithium diisopropylamide, sodium hexamethyldisilazane, lithium hexamethyldisilazane, potassium hexamethyldisilazane and the like. The reaction time and the solvent to be used are suitably determined according to the kind of base to be used. For example, in the case where lithium diisopropylamide is used, it is desirable to conduct the reaction at $+60°$ to $-100°$ C. in diethyl ether or tetrahydrofuran. When sodium hexamethyldisilazane is used, it is desirable to carry out the reaction in tetrahydrofuran, dioxane, benzene or toluene at room temperature to 110° C. The base is used in 1 to 10 times, preferably 1 to 5 times, the amount equivalent to the compound (VII).

g) The compound (VIII) is treated in the presence of an acid to hydrolyze the group $—OR^2$ thereof and then treated in the presence of a base for decyanohydrogenation to obtain an optically active 2-methylenecyclopentanone derivative (IX). The hydrolysis of $—OR^2$ is effected by a known method. For example, this reaction can be conducted in a water-containing solvent at a temperature of 0° to 100° C. using an acid such as hydrochloric acid, p-toluenesulfonic acid or acetic acid, acidic ion exchange resin, Lewis acid such as trifluoroboron etherate, zinc bromide or aluminum chloride, or weakly acidic substance such as pyridine-p-toluenesulfonic acid salt. When the protective group $R^2$ is silyl, it is also possible to remove the protective group with use of tetra-n-butyl ammonium fluoride or like quaternary ammonium fluoride salt. When the protective group $R^2$ is aralkyl, hydrogenation decomposition with use of palladium is also an effective method.

The decyanohydrogenation is conducted using at least an equivalent amount of sodium hydroxide, potassium hydroxide, sodium hydrogencarbonate, potassium carbonate or like inorganic base, or ammonia, triethylamine, pyridine, 4-dimethylaminopyridine or like organic base.

h) The compound (IX) is reacted with an organozinc compound or organocopper compound ($R^5M$) separately prepared to introduce an alpha-chain into the compound (IX), and the resulting enolate is reacted with an organoselenium compound or organosulfur compound ($R^6ZY$) to give an optically active cyclopentanone derivative (X). The derivative (X) is oxidized with an oxidizing agent, such as hydrogen peroxide or organic peracid, followed by an elimination reaction at a temperature of 0° to 150° C. to obtain a known optically active cyclopentenone derivative (XI) which is an intermediate for preparing a prostaglandin.

The organozinc compound or organocopper compound $R^5M$ is prepared by the following method. The organocopper compound is prepared by lithiating a compound $R^5X^2$ (wherein $X^2$ is chlorine, bromine, or like halogen atom), for example, with methyllithium, sec-butyllithium, tert-butyllithium or like organolithium compound or metallic lithium, or reacting the compound $R^5X^2$ with metallic magnesium to obtain a Grignard reagent, and treating the resulting compound with cuprous cyanide, cuprous iodide or separately prepared (2-thienyl)Cu(CN)Li. The organozinc compound can be prepared by reacting the tetramethylethylenediamine complex of zinc chloride with two equivalents of methyllithium to obtain dimethylzinc, and adding a reaction mixture obtained by lithiating the compound $R^5X^2$ to the product. The reaction for preparing the organometallic compound $R^5M$ can be conducted at a temperature of $-100°$ to $0°$ C. in an inert solvent, such as n-hexane, toluene or like hydrocarbon, diethyl ether, tetrahydrofuran, dioxane or like ether, or a mixture of such solvents.

i) The compound (XI) can be converted to an aldehyde or alcohol by removing the acetal, silyl, alkyloxyalkyl or like protective group from the group $R^5$ thereof A prostaglandin derivative can be prepared from the compound (XI) by a known process (F. S. Alvarez et al., J. Am. Chem. Soc., 94, 7823(1972); A. F. Kluge et al, J. Am. Chem. Soc., 94, 7828, 9256(1972); C. J. Sih et al., J. Am., Chem. Soc., 97, 857, 865 (1975)).

EXAMPLES

To clarify the technical features of the present invention, the present invention will be described in greater detail with reference to the following examples.

Preparation of compounds (II)

In an argon atmosphere with stirring, n-butyllithium was added dropwise over a period of 20 minutes to a solution of 9.35 g (44.9 mmoles) of 2-bromo-3,3-diethoxypropene in 80 ml of anhydrous tetrahydrofuran cooled to $-78°$ C., and the mixture was further stirred at $-78°$ C. for 40 minutes to prepare a vinyllithium solution.

On the other hand, 5.31 g (37.4 mmoles) of trifluoroboron etherate was added dropwise to a solution of 3.46 g (37.4 mmoles) of optically active (S)-epichlorohydrin (at least 98.5% in chemical purity, at least 99% in optical purity) in 70 ml of anhydrous tetrahydrofuran cooled to $-78°$ C., with stirring in an argon atmosphere, followed by further stirring for 10 minutes.

The vinyllithium solution previously prepared was added dropwise to the epichlorohydrin at $-78°$ C. over a period of 35 minutes, and the mixture was further stirred for 20 minutes. With vigorous stirring, the resulting reaction mixture was poured into a saturated aqueous solution of ammonium chloride which was precooled. The aqueous layer was subjected to extraction with ether six times, the ethereal extract was washed with a saturated aqueous ammonium chloride solution twice and with a saturated sodium chloride aqueous solution twice and then dried over anhydrous magnesium sulfate. The dried extract was distilled in a vacuum to remove the solvent, giving 6.97 g (yield 84%) of an optically active 4-hydroxy-2-methylenepentane derivative (II-a) represented by the following chemical formula.

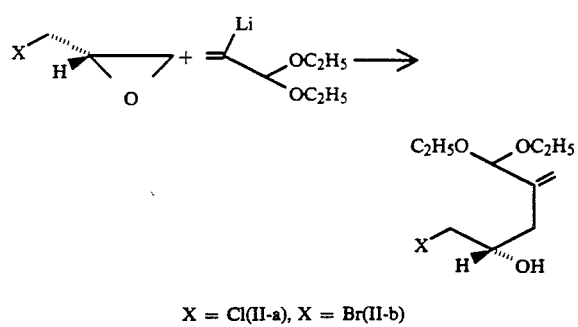

X = Cl(II-a), X = Br(II-b)

NMR (CDCl$_3$) δ: 1.23 (6H, t, J=7.0 Hz, CH$_3$), 2.34–2.52 (2H, m, CH$_2$), 3.25–4.17 (9H, m, CH$_2$O, CH$_2$Cl, CH, OH, 4.70 (1H, s, OCH-O), 5.14–5.50 (2H, m, =CH$_2$).

The same procedure as above was repeated except that optically active (S)-epibromohydrin was used instead of optically active (S)-epichlorohydrin to obtain an optically active 4-hydroxy-2-methylenepentane derivative (II-b) represented by the above chemical formula.

NMR (CDCl$_3$) δ: 1.23 (6H, t, J=7.0 Hz, CH$_3$), 2.34–2.55 (2H, m, CH$_2$), 3.29–3.80 (8H, m, CH$_2$O, CH$_2$Br, CH), 3.80–4.14 (1H, m, OH), 4.71 (1H, s, OCH-O), 5.14–5.32 (2H, m, =CH$_2$).

Preparation of compounds (III)

Imidazole (6.43 g, 94.5 mmoles) was added drop-wise to a solution of 6.96 g of the above 4-hydroxy-2-methylenepentane derivative (II-a) in 10 ml of N,N-dimethylformamide at 0 ° C. with stirring, 14.07 g (51.3 mmoles) of tert-butyldiphenylsilyl chloride was then added dropwise to the solution, followed by stirring on a water bath overnight. The reaction mixture was thereafter neutralized with 3N hydrochloric acid, the aqueous layer was subjected to extraction with ether three times, and the extract was washed with a saturated aqueous solution of sodium bicarbonate twice and then with saturated aqueous solution of sodium chloride three times and dried over anhydrous magnesium sulfate. The solvent was distilled off in a vacuum, giving 19.96 g of an optically active 2-methylenepentane derivative (III-a) having protected hydroxyl and represented by the following chemical formula.

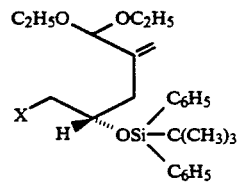

X = Cl(III-a)
X = Br(III-b)

IR (neat): 3400, 1640, 1050 cm$^{-1}$.

The same procedure as above was repeated except that the optically active compound (II-b) wherein X is Br was used in place of the optically active 4-hydroxy-2-methylenepentane derivative (II-a) to obtain an optically active compound (III-b) represented by the above chemical formula.

Preparation of compounds (IV)

A 19.87 g quantity of the optically active 2-methylenepentane derivative (III-a) was dissolved in 120 ml of 80% aqueous solution of methanol, and the solution was heated with stirring for 1 hour with the addition of 10.09 g of copper sulfate. The reaction mixture was passed through Celite for filtration. With addition of 300 ml of benzene, the filtrate was subjected to azeotropic distillation to remove methanol and water. The residue was subjected to extraction with ether, and the ethereal extract was washed with a saturated aqueous solution of sodium bicarbonate. The aqueous layer was subjected to extraction with ether six times, and the extract was washed with an aqueous solution of sodium chloride, dried over anhydrous magnesium sulfate and distilled in a vacuum to remove the solvent, giving 18.66 g of an optically active 2-methylenepentanal derivative (IV-a) represented by the following chemical formula.

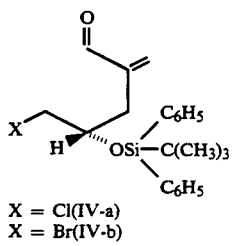

X = Cl(IV-a)
X = Br(IV-b)

NMR (CDCl$_3$) δ: 1.07 (9H, s, CH$_3$) 2.49–2.71 (2H, m, CH$_2$) 3.34 (2H, d, J=5.0 Hz, CH$_2$), 3.94–4.26 (1H, m, CH), 5.99 (1H, s, =CH), 6.24 (1H, s, =CH), 7.29–7.91 (10H, m, C$_6$H$_5$), 9.94 (1H, s, CHO).

IR (neat): 1685, 1480, 1100, 700 cm$^{-1}$.

The same procedure as above was repeated except that the optically active compound (III-b) wherein X is Br was used in place of the optically active 2-methylenepentane derivative (III-a) to obtain an optically active (IV-b) represented by the above chemical formula.

NMR (CDCl$_3$) δ:1.07 (9H, s, CH$_3$), 2.43–2.83 (2H, m, CH$_3$), 3.21 (2H, d, J=5.0 Hz, CH$_2$), 3.86–4.23 (1H, m, CH), 5.99 (1H, br s, =CH), 6.26 (1H, br s, =CH), 7.29–7.91 (10H, m, C$_6$H$_5$), 9.94 (1H, s, CHO).

IR (neat): 1685, 1580, 1100, 700 cm$^{-1}$.

Preparation of compounds (VI)

In an argon atmosphere, a catalytic quantity of potassium cyanide complex of 18-Crown ether was added to 18.66 g of the optically active 2-methylenepentanal derivative (IV-a), and 3.65 g (36.8 mmoles) of trimethylsilyl cyanide was added dropwise to the mixture with stirring. The reaction mixture was further stirred on a water bath for 1 hour, diluted with 100 ml of tetrahydrofuran, and stirred for 20 minutes with addition of 30 ml of 1N hydrochloric acid. The aqueous layer was subjected to extraction with ether six times, and the extract was washed with water, then dried over anhydrous magnesium sulfate and distilled in a vacuum to remove the solvent, giving an optically active 1-cyano-2-methylenepentane derivative (VI-a) in the form of a crude product and represented by the following chemical formula. The crude product was subjected to silica gel column chromatography (n-hexane: ether=8.1) to obtain 6.14 g of a purified product. The yield was 47.4% based on the compound (II-a). A 2.80 g quantity of the material compound (IV-a) was recovered from the process.

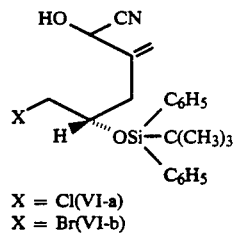

X = Cl(VI-a)
X = Br(VI-b)

NMR (CDCl$_3$) 1.0–1.17 (9H, d, CH$_3$), 2.51–2.86 (2H, m, CH$_2$), 3.00–3.57 (3H, m, CH$_2$, CH), 3.91–4.23 (1H, m, CH), 4.71–4.96 (1H, m, OH), 5.21–5.63 (2H, m, =CH$_2$), 7.25–7.91 (1H, m, CH).

The same procedure as above was repeated except that the optically active compound (IV-b) wherein X is Br was used in place of the optically active 2-methylenepentanal derivative (IV-a) to obtain an optically active compound (VI-b).

NMR (CDCl$_3$) δ: 1.0–1.32 (9H, m, CH$_3$), 2.55–3.67 (5H, m, CH$_2$, CH), 3.90–4.21 (1H, m, CH), 4.84 (1H, s, OH), 5.18–5.67 (2H, m, =CH$_2$), 7.28–7.85 (10H, m, C$_6$H$_5$).

Preparation of compounds (VII)

A catalytic quantity of p-toluenesulfonic acid was added to a solution of 6.14 g (14.8 mmoles) of the optically active 1-cyano-2-methylenepentane derivative (VI-a) in 90 ml of anhydrous benzene in an argon atmosphere, and 1.18 g (16.3 mmoles) of ethyl vinyl ether was added dropwise to the solution on a water bath with stirring. The reaction mixture was further stirred for 40 minutes and neutralized with a precooled saturated aqueous solution of sodium bicarbonate. The aqueous layer was subjected to extraction with ether four times, and the extract was washed with an aqueous solution of sodium chloride, then dried over anhydrous magnesium sulfate and distilled in a vacuum to remove the solvent, giving 6.68 g of an optically active 1-cyano-2-methylenepentane derivative (VII-a) represented by the following chemical formula.

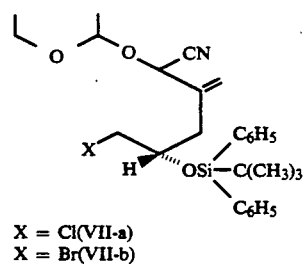

X = Cl(VII-a)
X = Br(VII-b)

NMR (CDCl$_3$) δ0.93–1.43 (15H, m, CH$_3$), 2.35–2.74 (2H, m, CH$_2$), 3.23–3.77 (4H, m, CH$_2$), 3.89–4.11 (1H, m, CH), 4.34–5.03 (2H, m, CH), 5.19 (1H, br s, =CH), 5.43–5.63 (1H, m, =CH), 7.29–7.91 (10H, m, C$_6$H$_5$).

The same procedure as above was repeated except that the optically active compound (VI-b) wherein X is Br was used in place of the optically active 1-cyano-2-methylenepentane derivative (VI-a) to obtain an optically active compound (VII-b) represented by the above chemical formula.

NMR (CDCl₃) δ:0.93-1.43 (15H, m, CH₃), 2.37-2.74 (2H, m, CH₂), 3.09-3.77 (4H, m, CH₂, CH), 3.89-4.23 (1H, m, CH), 4.60-5.14 (2H, m, CH), 5.14-5.71 (2H, m, =CH₂), 7.31-7.91 (10H, m, C₆H₅).

IR (neat): 1700(C=C), 1110, 1050, 940, 830, 740, 700 cm⁻¹.

Preparation of compounds (VIII)

A 10.3 ml quantity of benzene solution of sodium hexamethyldisilazane (concentration: 0.66N) was added to 50 ml of anhydrous tetrahydrofuran in an argon atmosphere. A solution of 1.23 g of the optically active 1-cyano-2-methylenepentane derivative (VII-a) in 20 ml of anhydrous tetrahydrofuran was added dropwise to the mixture at 50° C. over a period of 70 minutes with stirring. With vigorous stirring, the reaction mixture was poured into a precooled saturated aqueous solution of ammonium chloride, followed by extraction with ether five times. The extract was washed with 1N hydrochloric acid and then with an aqueous solution of sodium chloride and purified by silica gel column chromatography (n-hexane:ether=20:1), affording 756 mg of an optically active 2-methylenecyclopentanecyanohydrin derivative (VIII) represented by the following chemical formula. The yield from the compound (VI-a) was 61.6%.

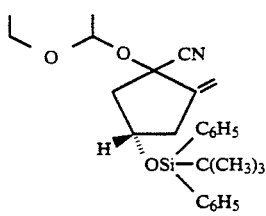

(VIII)

NMR (CDCl₃) δ: 0.93-1.57 (15H, m, CH₃), 2.06-2.71 (4H, m, CH₂), 3.23-3.86 (1H, m, CH), 4.14-4.60 (1H, m, CH), 4.69-5.11 (1H, m, CH), 5.11-5.37 (1H, m, CH), 5.37-5.66 (1H, m, CH), 7.31-7.90 (10H, m, C₆H₅).

The same procedure as above was repeated except that the optically active compound (VII-b) wherein X is Br was used in place of the optically active 1-cyano-2-methylenepentane derivative (VII-a), whereby an optically active compound (VIII) was obtained in a yield approximate to the above.

Preparation of compound (IX)

A catalytic quantity of pyridine p-toluenesulfonic acid salt was added to a solution of 756 mg (1.68 mmoles) of the optically active 2-methylenecyclopentanecyanohydrin derivative (VIII) in 30 ml of anhydrous methanol in an argon atmosphere, followed by refluxing for 1.2 hours. The solvent was distilled off in a vacuum, 25 ml of anhydrous tetrahydrofuran and 10 ml of saturated aqueous solution of sodium bicarbonate were thereafter added to the residue at room temperature, and the mixture was stirred for 1.5 hours. Ether was added to the reaction mixture for extraction, and the extract was washed with an aqueous solution of sodium chloride. The aqueous layer was further subjected to extraction with ether five times. The extracts were combined together, washed with 1N hydrochloric acid and then with an aqueous solution of sodium chloride and thereafter dried. The solvent was distilled off in a vacuum, and the residue was purified by silica gel column chromatography (n-hexane:ether=40:1), giving 307.5 mg (yield 52.2%) of an optically active 2-methylenecyclopentanone derivative (IX) represented by the following chemical formula.

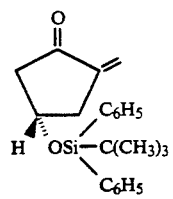

(IX)

IR (neat): 1730, 1645, 1100, 730 cm⁻¹.

¹HNMR (CDCl₃) δ: 1.04 (9H, s, CH₃), 2.42 (2H, d, J=5.0 Hz, CH₂), 2.72 (2H, quint, 2.4 Hz, CH₂), 4.47 (1H, quint, 5.0 Hz, CH), 5.29 (1H, dt, J=2.4 Hz, 1.5 Hz, =CH), 6.03 (1H, dt, J=2.4 Hz, 1.5 Hz, =CH), 7.31-7.91 (10H, m, C₆H₅).

¹³CNMR (CDCl₃) δ: 19.06, 26.79, .40.02, 48.26, 68.51, 118.03, 7.70, 127.76, 129.82, 129.86, 133.50, 133.73, 135.64, 143.22, 204.40.

Preparation of compound (X)

A solution of 247.8 mg (0.831 mmole) of a vinyl iodide derivative represented by the following chemical formula

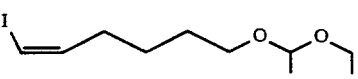

(XII)

in 7 ml of n-hexane was cooled to −78° C. in an argon stream. This compound is known by J. Am. Chem. Sco.,97 4745 (1975). Using a syringe, tert-butyllithium was added dropwise to the solution with stirring over a period of 5 minutes, followed by stirring at the same temperature for 90 minutes to obtain a vinyllithium compound represented by the following chemical formula

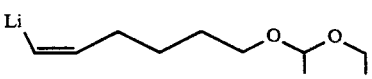

On the other hand, 230.8 mg (0.914 mmole) of tetramethylethylenediamine complex of zinc chloride was placed in an argon stream into a three-necked flask, 7 ml of anhydrous tetrahydrofuran was further placed in, and the mixture was cooled to −20° C. with stirring. Using a syringe, 1.07 ml of 1.7N solution of methyllithium (1.828 mmoles) in n-hexane was added dropwise to the mixture over a period of 3 minutes, and the reaction mixture was stirred for a further period of 10 minutes and thereafter cooled to −80 ° C.

A solution of the above vinyllithium compound was added dropwise to the resulting solution at −78 ° C. over a period of 5 minutes using a bridge, followed by stirring at −78 ° C. to −60° C. for 1 hour.

A 7 ml quantity of anhydrous tetrahydrofuran solution of 223.5 mg (0.6376 mmole) of the optically active 2-methylenecyclopentanone derivative (IX) was added dropwise to the reaction mixture at −78 ° C. with full stirring over a period of 40 minutes. The container used was washed with 2 ml of anhydrous tetrahydrofuran, and the washings were added to the reaction mixture with stirring over a period of 10 minutes, followed by continued stirring at −78° C. for 30 minutes.

A 7 ml quantity of anhydrous tetrahydrofuran solution of 996.0 mg (3.197 mmoles) of diphenyl diselenide was added to the resulting reaction mixture at −78° C. with vigorous stirring using a syringe, followed by stirring at −50 ° C. for 30 minutes. The reaction mixture was thereafter poured into a cooled saturated aqueous solution of ammonium chloride with vigorous stirring. The aqueous layer was subjected to extraction with ether six times. The combined ethereal extract was washed with a saturated aqueous solution of sodium chloride twice, then dried over anydrous magnesium sulfate and filtered. The solvent was distilled off from the filtrate. The resulting crude product was purified by silica gel column chromatography (n-hexane:ether=5:1), giving 220.1 mg (yield 50.9%) of an optically active 2-phenylselenocyclopentanone derivative (X) represented by the following chemical formula.

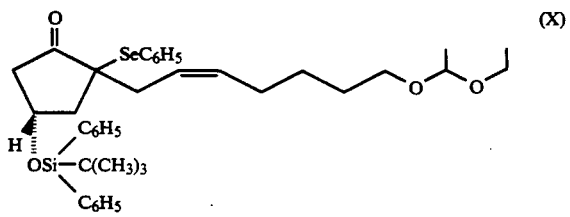

NMR (CDCl$_3$) δ: 1.04 (9H, s, CH$_3$), 1.04–1.74 (12H, m, CH$_3$, CH$_2$), 1.82–2.86 (6H, m, CH$_2$CO, CH$_2$C=C), 3.30–3.82 (4H, m, CH$_2$O), 4.34–4.78 (2H, m, OCH), 5.15–5.50 (2H, m =CH), 7.10–7.70 (15H, m, C$_6$H$_5$).

IR (neat): 1730, 1105, 740, 700 cm$^{-1}$.

Preparation of compound(XI)

A 115.7 mg quantity (0.170 mmole) of the optically active 2-phenylselenocyclopentanone derivative (X) was dissolved in 15 ml of tetrahydrofuran. To the solution thereafter cooled to 0° C. was added at a time 0.14 ml (156.1 mg, 1.90 mmoles) of 30% hydrogen peroxide with stirring. The reaction mixture was slowly returned to room temperature and further stirred at room temperature for 3 hours. The reaction mixture was diluted with ether, and the ethereal layer was separated off and washed with a saturated aqueous solution of sodium chloride. The aqueous layer was further subjected to extraction five times. The ethereal layers were combined together, washed with a saturated aqueous solution of sodium chloride again and thereafter dried over anhydrous magnesium sulfate. The solvent was distilled off in a vacuum from the dry extract. The residue, which was an oily product, was purified by silica gel chromatography (n-hexane:ether=5:1) and further purified by high performance liquid chromatography (silica gel "Si-160," 7.6 cm (diam.)×30 cm, n-hexane:ethyl acetate=1:4), giving 40.6 mg (yield 45.9%) of an optically active cyclopentenone derivative (XI) represented by the following chemical formula and 25.8 mg of a by-product of undetermined structure.

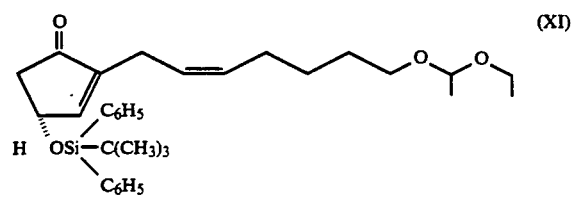

NMR (CDCl$_3$) δ: 1.07 (9H, s, CH$_3$), 1.07–1.79 (12H, m, CH$_2$, CH$_3$), 1.87–2.26 (2H, m, CH$_2$), 2.34–2.54 (2H, m, CH$_2$), 2.70–2.94 (2H, m, CH$_2$), 3.18–3.82 (4H, m, CH$_2$), 4.66 (1H, q, J=5.5 Hz, CH), 4.75–4.98 (1H, m, CH), 5.44 (1H, m, =CH), 6.88–7.02 (1H, m, =CH), 7.26–7.78 (10H, m, C$_6$H$_5$).

IR (neat): 1715, 1105, 700 cm$^{-1}$.

To a solution of 31.9 mg (0.06 mmole) of the optically active cyclopentenone derivative (XI) in 2 ml of anhydrous methanol was added a catalytic quantity of p-toluenesulfonic acid in an argon stream with ice-cooling. The reaction mixture was stirred with ice-cooling for 1 hour and 20 minutes and thereafter stirred at room temperature for 1 hour. The reaction mixture was then neutralized with a precooled saturated aqueous solution of sodium bicarbonate. The aqueous layer was subjected to extraction with dichloromethane five times, and the extracts were combined together, washed with a saturated aqueous solution of sodium chloride twice and thereafter dried over anhydrous magnesium sulfate. The solvent was distilled off from the dry extract in a vacuum, and an oily product obtained as the residue was subsequently purified by silica gel column chromatography (n-hexane:ether=1:1), giving 24.8 mg (yield 90.2%) of an optically active cyclopentenone derivative (XII) represented by the following chemical formula.

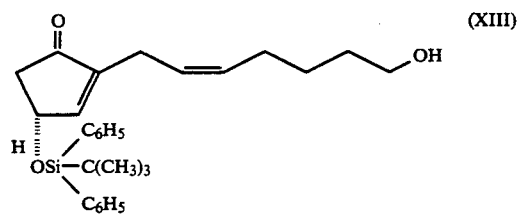

[α]$^{25}_D$= +31.85° (C=0.496, methanol).

$^1$HNMR (CDCl$_3$) δ: 1.07 (9H, s, CH$_3$), 1.15–1.79 (5H, m, CH$_2$, OH), 1.87–2.27 (2H, m, CH$_2$), 2.06 (2H, br q, J=6.4 Hz, CH$_2$), 2.87 (2H, br d, J=6.0 Hz, CH$_2$), 3.62 (2H, t, J=6.4 Hz, CH$_2$), 4.75–4.96 (1H, m, CH), 5.30–5 55 (2H, m, =CH), 6.93–6.98 (1H, m, =CH), 7.27–7.75 (10H, m, C$_6$H$_5$).

$^{13}$CNMR (CDCl$_3$) δ: 19.72, 23.24, 26.22, 27.47, 32.89, 43.94, 46.00, 63.34, 70.54, 125.38, 128.41, 130.58, 132.64, 134.26, 136.26, 146.51, 157.23, 177.87.

IR (neat): 3400, 1710, 1110, 1070, 780, 700 cm$^{-1}$.

What we claim is:

1. A process for preparing an optically active cyclopentenone compound of the formula

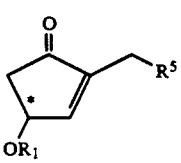

which comprises oxidizing an optically active cyclopentanone compound of the formula

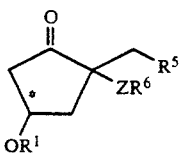

wherein R¹ is a protective group for hydroxyl, R⁵ is straight-chain or branched-chain alkyl, alkenyl, alkynyl or alkylaryl having 5 to 22 carbon atoms optionally containing oxygen, sulfur or silicon in the chain, R⁶ is alkyl, aryl or heterocyclic group which may have a substituent, Z is selenium or sulfur, and * designates an asymmetric carbon, with an oxidizing agent, and subsequently subjecting the oxidized compound to an elimination reaction.

2. A process as defined in claim 1, wherein R¹ is silyl, R⁵ is

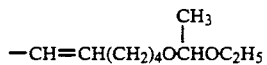

and R⁶ is phenyl.

3. A process for preparing an optically active cyclopentenone compound of the formula

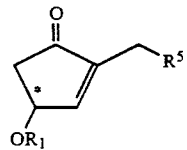

which comprises reacting an optically active 2-methylenecyclopentanone compound of the formula

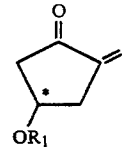

wherein R¹ is a protective group for hydroxyl, with an organozinc or copper compound represented by the formula, R⁵M wherein R⁵ is straight-chain or branched-chain alkyl, alkenyl, alkynyl or alkylaryl having 5 to 22 carbon atoms optionally containing oxygen, sulfur or silicon in the chain, causing an organoselenium or sulfur compound represented by the formula R⁶ZY to act on the resulting enolate to obtain an optically active cyclopentanone compound represented by the formula

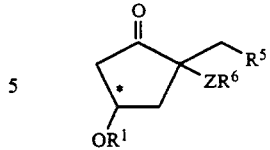

wherein R⁶ is alkyl, aryl or heterocyclic group which may have a substituent, Z is selenium or sulfur, and the symbol * represents an asymmetric carbon atom, M is (CH₃)₂ZnLi, Cu(CN)Li, Cu(CN)MgBr, Cu(CN)MgCl, Cu(N)MgI, (CuLi)₁/₂, (2-thienyl)-Cu(CN)Li₂ or Cu(P-butyl₃)ₙ, wherein n is 2 or 3, and Y is a halogen atom or ZR⁶.

4. A process as defined in claim 3 wherein R¹ is silyl, R⁵ is

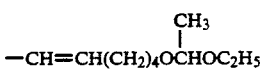

and R⁶ is phenyl.

5. A process for preparing an optically active cyclopentanone compound of the formula

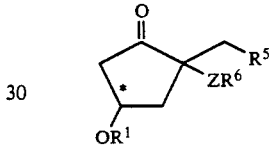

wherein R¹ is a protective group for hydroxyl, R⁵ is straight-chain or branched-chain alkyl, alkenyl, alkynyl or alkylaryl having 5 to 22 carbon atoms and optionally containing oxygen, sulfur or silicon in the chain, R⁶ is alkyl, aryl or heterocyclic group which may have a substituent, Z is selenium or sulfur, and the symbol * represents an asymmetric carbon, which comprises reacting an optically active 2-methylenecyclopentanone compound represented by the formula

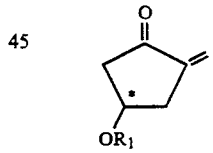

with an oxidizing agent, and subsequently subjecting the oxidized compound to an elimination reaction with an organozinc or copper compound represented by the formula R⁵M, wherein M is (CH₃)₂ZnLi, Cu(CN)Li, Cu(CN)MgBr, Cu(CN)MgCl, Cu(N)MgI, (CuLi)₁/₂,(2-thienyl)Cu(CN)Li₂ or Cu(Pbutyl₃)ₙ, wherein n is 2 or 3 and Y is a halogen atom or ZR⁶, and causing an organoselenium or sulfur compound represented by the formula R⁶ZY to act on the resulting enolate.

6. A process as defined in claim 5, wherein R¹ is silyl, R⁵ is

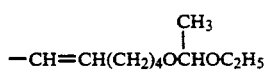

and R⁶ is phenyl.

* * * * *